(12) United States Patent
Kikuiri

(10) Patent No.: US 9,869,650 B2
(45) Date of Patent: Jan. 16, 2018

(54) PATTERN INSPECTION APPARATUS

(71) Applicant: NuFlare Technology, Inc., Yokohama-shi (JP)

(72) Inventor: Nobutaka Kikuiri, Koganei (JP)

(73) Assignee: NuFlare Technology, Inc., Yokohama-shi (JP)

( * ) Notice: Subject to any disclaimer, the term of this patent is extended or adjusted under 35 U.S.C. 154(b) by 0 days.

(21) Appl. No.: 15/497,425

(22) Filed: Apr. 26, 2017

(65) Prior Publication Data

US 2017/0315070 A1   Nov. 2, 2017

(30) Foreign Application Priority Data

Apr. 28, 2016   (JP) .................. 2016-090746

(51) Int. Cl.
 *G01N 23/00* (2006.01)
 *G01N 23/225* (2006.01)
 *G01B 15/00* (2006.01)
(52) U.S. Cl.
 CPC ......... *G01N 23/2251* (2013.01); *G01B 15/00* (2013.01); *G01N 2223/6116* (2013.01)

(58) Field of Classification Search
 CPC ....... G01N 23/2251; G01N 2223/6116; G01B 15/00
 USPC ................. 250/306, 307, 310, 311
 See application file for complete search history.

(56) References Cited

U.S. PATENT DOCUMENTS

2005/0285037 A1* 12/2005 Nakamura .............. H01J 37/04
                                                          250/311
2011/0297827 A1* 12/2011 Asai ...................... H01J 37/244
                                                          250/310

FOREIGN PATENT DOCUMENTS

JP         2002-208371        7/2002

* cited by examiner

*Primary Examiner* — Michael Maskell
(74) *Attorney, Agent, or Firm* — Oblon, McClelland, Maier & Neustadt, L.L.P.

(57) ABSTRACT

A pattern inspection apparatus includes a column to scan a substrate on which a pattern is formed, using multi-beams composed of a plurality of electron beams, a stage to mount the substrate thereon and to be movable, a detector to detect secondary electrons emitted from the substrate because the substrate is irradiated with the multi-beams, and a drive mechanism to move the detector in order to follow movement of the stage.

10 Claims, 10 Drawing Sheets

PATTERN INSPECTION APPARATUS

CROSS-REFERENCE TO RELATED APPLICATION

This application is based upon and claims the benefit of priority from the prior Japanese Patent Application No. 2016-090746 filed on Apr. 28, 2016 in Japan, the entire contents of which are incorporated herein by reference.

BACKGROUND OF THE INVENTION

Field of the Invention

Embodiments of the present invention relate generally to a pattern inspection apparatus. More specifically, for example, embodiments of the present invention relate to an inspection apparatus which inspects patterns by acquiring a secondary electron image of a pattern image emitted due to irradiation by an electron beam.

Description of Related Art

In recent years, with the advance of high integration and large capacity of large-scale integration (LSI) circuits, the line width (critical dimension) required for circuits of semiconductor elements is becoming progressively narrower. Such semiconductor elements are manufactured by circuit formation of exposing and transferring a pattern onto a wafer by means of a reduced projection exposure apparatus known as a stepper while using an original or "master" pattern (also called a mask or a reticle, hereinafter generically referred to as a mask) with a circuit pattern formed thereon.

Since LSI manufacturing requires a tremendous amount of manufacturing cost, it is crucial to improve its yield. However, as typified by a 1-gigabit DRAM (Dynamic Random Access Memory), the scale of patterns configuring an LSI has become on the order of nanometers from submicrons. In recent years, with miniaturization of dimensions of LSI patterns formed on a semiconductor wafer, dimension to be detected as a pattern defect has become extremely small. Therefore, a pattern inspection apparatus for inspecting defects of ultrafine patterns transferred and exposed onto a semiconductor wafer needs to be more highly accurate. Further, one of major factors that decrease the yield of the LSI manufacturing is due to pattern defects on the mask used for exposing and transfer printing an ultrafine pattern onto a semiconductor wafer by the photolithography technology. Therefore, a pattern inspection apparatus for inspecting defects on a transfer mask used in manufacturing LSI needs to be more highly accurate.

As an inspection method, there is known a method of comparing an optical image obtained by imaging a pattern formed on a substrate (target object or "sample") such as a semiconductor wafer and a lithography mask at a predetermined magnification by using a magnification optical system with design data or an optical image obtained by imaging the same pattern on the target object. For example, the methods described below are known as pattern inspection methods: the "die-to-die inspection" method that compares data of optical images of identical patterns at different positions on the same mask; and the "die-to-database inspection" method that inputs, into an inspection apparatus, writing data (design pattern data) generated by converting pattern-designed CAD data to a writing apparatus specific format to be input to the writing apparatus when a pattern is written on the mask, generates a design image data (reference image) based on the input writing data, and compares the generated design image with an optical image (serving as measurement data) obtained by imaging the pattern. In such inspection methods for use in the inspection apparatus, a substrate to be inspected (an inspection substrate or "object" to be examined) is placed on the stage so that a light flux may scan the substrate (target object) as the stage moves in order to perform an inspection. Specifically, the substrate to be inspected is irradiated with a light flux from the light source through the illumination optical system. The light transmitted through the inspection substrate or reflected therefrom forms an image on a sensor through the optical system. The image captured by the sensor is transmitted as measurement data to the comparison circuit. After performing positioning between images, the comparison circuit compares measurement data with reference data in accordance with an appropriate algorithm, and determines that there exists a pattern defect if the compared data are not identical.

The pattern inspection apparatus described above acquires an optical image by irradiating an inspection substrate with a laser beam in order to capture a transmission image or a reflection image of a pattern formed on the substrate. On the other hand, there has been developed an inspection apparatus which acquires a pattern image by irradiating an inspection substrate with multiple electron beams in order to detect a secondary electron corresponding to each beam emitted from the substrate (e.g., refer to Japanese Patent Application Laid-open (JP-A) No. 2002-208371). The pattern inspection apparatus using an electron beam(s), such as multiple electron beams or a single electron beam, scans each small region of the inspection substrate with beams in order to detect a secondary electron. In that case, a so-called "step and repeat" operation is performed in which the position of the substrate to be inspected is fixed during the beam scanning, and then, after the scanning, the substrate to be inspected is moved to a next region. In pattern inspection, since it is necessary to inspect almost the whole surface of the substrate to be inspected, the substrate is usually placed on a heavy stage driven by a motor, etc. Then, it is difficult to attenuate such a heavy stage after having been moved. As described above, since almost the whole surface of the inspection substrate needs to be inspected, the stage moves a long stroke distance. For the stage which moves through a long stroke, a large attenuation mechanism is needed to perform attenuation after the moving. Moreover, in order to attenuate, in a short period of time, the stage being heavy and moving through a long stroke, a still larger attenuation mechanism is needed. However, it is difficult to arrange a large attenuation mechanism in a limited space. Therefore, an attenuation mechanism arrangeable in the limited space is used, but, in such a case, it takes time for statically settling (stabilizing) the stage to stop at a position within a predetermined accuracy after the step movement of the stage. Supposing that the settling time needs 20 ms, for example, there is a problem in that the time obtained by "the number of times of performing step-and-repeat movement"× "20 ms" is needed as a useless time during which no actual inspection is performed. While at the same time, it is required to reduce the inspection time.

BRIEF SUMMARY OF THE INVENTION

According to one aspect of the present invention, there is provided a pattern inspection apparatus including a column configured to scan a substrate on which a pattern is formed, using multi-beams composed of a plurality of electron beams, a stage configured to mount the substrate thereon and to be movable, a detector configured to detect secondary electrons emitted from the substrate because the substrate is irradiated with the multi-beams, and a drive mechanism configured to move the detector in order to follow movement of the stage.

According to another aspect of the present invention, there is provided a pattern inspection apparatus including a column configured to scan a substrate on which a pattern is formed, using multi-beams composed of a plurality of electron beams, a stage configured to mount the substrate thereon and to be movable, a plurality of detectors each configured to detect secondary electrons emitted from the substrate because the substrate is irradiated with the multi-beams, a plurality of drive mechanisms each configured to move a corresponding detector of the plurality of detectors in order to follow movement of the stage, and an image generation processing circuitry configured to combine each data detected by the plurality of detectors and to generate an image of the pattern.

DETAILED DESCRIPTION OF THE INVENTION

First Embodiment

Hereinafter, a first embodiment of the present invention describes a pattern inspection apparatus capable of reducing the time during which no inspection can be performed because of the "step and repeat" operation, in pattern inspection using electron beams.

Figure 1:
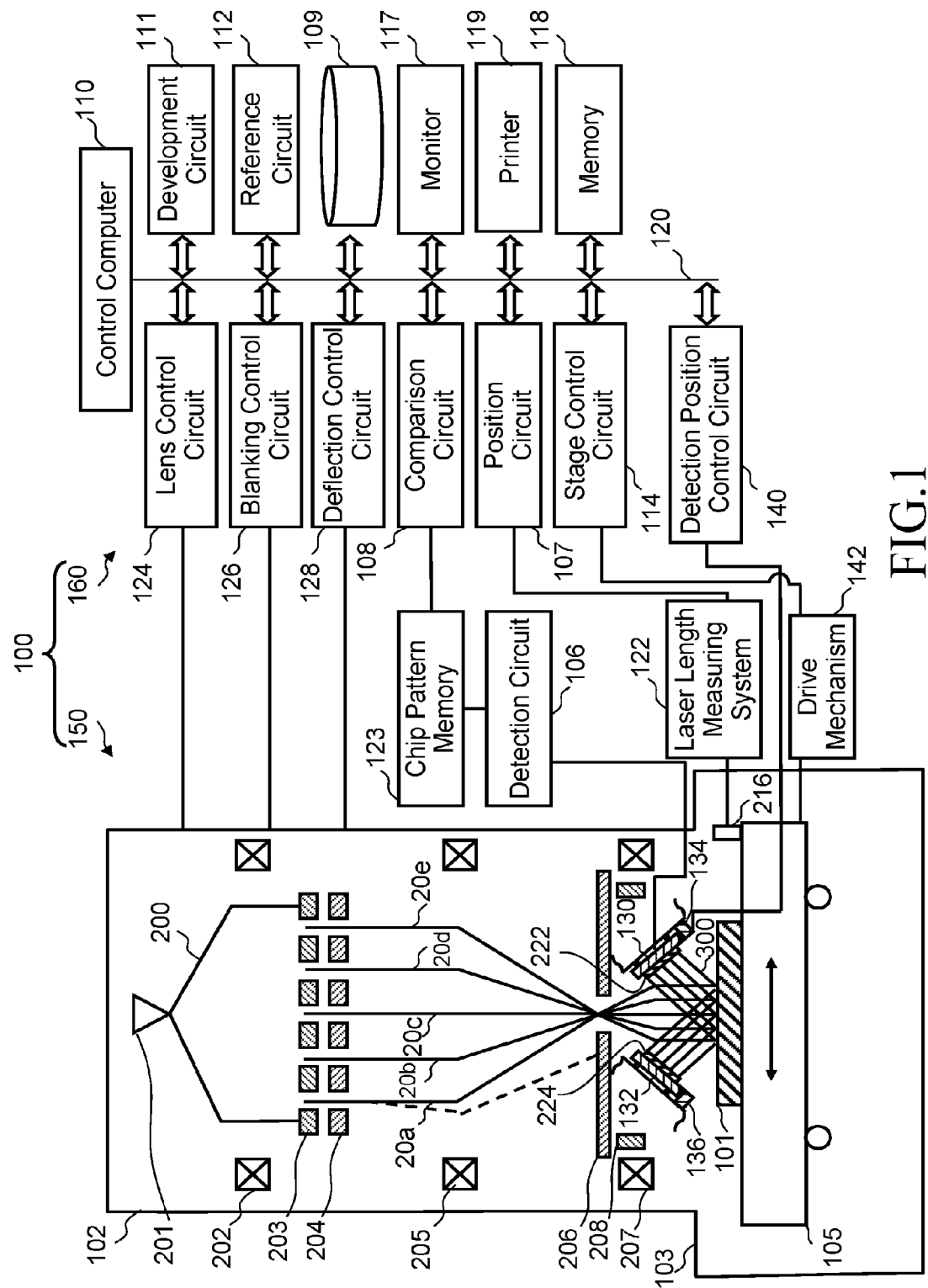
FIG. 1 is a conceptual diagram showing a configuration of a pattern inspection apparatus according to a first embodiment.

FIG. 1 is a conceptual diagram showing a configuration of a pattern inspection apparatus according to the first embodiment. In FIG. 1, an inspection apparatus 100 for inspecting patterns formed on the substrate is an example of a multi electron beam inspection apparatus. The inspection apparatus 100 includes an optical image acquisition unit 150 and a control system circuit 160 (control unit). The optical image acquisition unit 150 includes an electron beam column 102 (electron optical column), an inspection chamber 103, a detection circuit 106, a chip pattern memory 123, a stage drive mechanism 142, and a laser length measurement system 122. In the electron beam column 102, there are arranged an electron gun 201, an illumination lens 202, a shaping aperture array member 203, a blanking aperture array mechanism 204, a reducing lens 205, a limiting aperture member 206, an objective lens 207, a deflector 208, a plurality of detectors 222 and 224, a plurality of detector stages 130 and 132, and a plurality of drive mechanisms 134 and 136.

In the inspection chamber 103, there is arranged an XY stage 105 which is movable at least in the x-y directions. On the XY stage 105, there is placed a substrate 101 on which a plurality of chip patterns to be inspected are formed. The substrate 101 may be an exposure mask or a semiconductor substrate such as a silicon wafer as described above. The substrate 101 is placed, on the XY stage 105, with its pattern forming surface facing upward, for example. On the XY stage 105, there is arranged a mirror 216 which reflects a laser beam for measuring a laser length emitted from the laser length measurement system 122 arranged outside the inspection chamber 103. The detectors 222 and 224 are connected, at the outside of the electron beam column 102, to the detection circuit 106. The detection circuit 106 is connected to the chip pattern memory 123.

In the control system circuit 160, a control computer 110 is connected, through a bus 120, to a position circuit 107, a comparison circuit 108, a development circuit 111, a reference circuit 112, a stage control circuit 114, a lens control circuit 124, a blanking control circuit 126, a deflection control circuit 128, a detection position control circuit 140, a storage device 109 such as a magnetic disk drive, etc., a monitor 117, a memory 118, and a printer 119. The chip pattern memory 123 is connected to the comparison circuit 108. The XY stage 105 is driven by the stage control circuit 114 under the control of the control computer 110. The XY stage 105 can be moved by a drive system such as a three-axis (X, Y, and θ) motor, which drives the stage in the directions of x, y, and θ. For example, a step motor can be used as each of these X, Y, and θ motors (not shown). The XY stage 105 is movable in the horizontal direction and the rotation direction by the motors of the X-axis, Y-axis, and θ-axis. The movement position of the XY stage 105 is measured by the laser length measurement system 122, and supplied (transmitted) to the position circuit 107. The laser length measurement system 122 measures the position (length) of the XY stage 105 by receiving a catoptric light from the mirror 216, based on the principle of laser interferometry.

A plurality of detectors 222 and 224 are individually arranged on a corresponding one of a plurality of detector stages 130 and 132, above the XY stage 105, in a manner such that they surround the optical path of multi-beams to be described later, and each of their detection surfaces faces the intersection between the surface of the substrate 101 arranged on the XY stage 105 and the optical axis. For example, each of their detection surfaces is arranged to be inclined with respect to the surface of the substrate 101, which is arranged on the XY stage 105, at an angle from 15° to 75°, for example. More preferably, each of the detection surfaces is arranged to be inclined at an angle between 30° and 60°, for example, an angle 45°.

Although, here, the two detectors 222 and 224 are shown as an example, it is not limited thereto, and more detectors may further be arranged. In the case of arranging the two detectors 222 and 224, it is preferable that they are arranged at positions opposite each other with respect to the optical path of multi-beams, or at the positions each rotated by 90° about the optical axis of multi-beams as a fulcrum.

A plurality of detector stages 130 and 132, on which a plurality of detectors 222 and 224 are placed, are driven by the detection position control circuit 140 under the control of the control computer 110. In the case of FIG. 1, the detector 222 is placed on the detector stage 130, and the detector 224 is placed on the detector stage 132. A plurality of detector stages 130 and 132 can be moved by a corresponding one of the drive mechanisms 134 and 136 each including a three-axis (X, Y, and θ) drive system which drives in two dimensional directions (x, y, and θ directions) parallel to the detection surface of the detector placed on the stage 130 or 132. The drive mechanisms 134 and 136 should drive the detector stages 130 and 132 through a stroke approximately as much as twice the maximum amplitude occurring during settling time to stop the XY stage 105 to be described later, or through a stroke approximately as much as twice the maximum amplitude+α. The detectors 222 and 224 should detect a secondary electron in a region approximately as large as an irradiation region which can be irradiated with one time multi-beam irradiation. Therefore, the detection surface of each of the detectors 222 and 224 can be substantially smaller than the surface of the substrate 101. Therefore, the size of each of the detector stages 130 and 132 can also be substantially smaller than the XY stage 105. Accordingly, the drive system of each axis of a plurality of drive mechanisms 134 and 136 can also be substantially smaller than the drive mechanism 142 of the XY stage 105. Consequently, vibration/oscillation during the settling time in stopping the detector stages 130 and 132 can be disregarded. A piezoelectric element, for example, can be used for the drive system of each axis of a plurality of drive mechanisms 134 and 136. Using the piezoelectric element makes it possible to cope with high speed response.

Although, in the example described above, a plurality of drive mechanisms 134 and 136 can be individually driven in the three axial directions, it is not limited thereto. As to be described later, when the XY stage 105 moves in the step direction of the "step and repeat" operation performed in pattern inspection, vibration/oscillation occurring during settling time to stop the XY stage 105 mainly occurs in the step direction and the reverse direction to the step direction. Therefore, the beam irradiation position to the substrate 101 deviates (shifts) in the direction contrary to the vibration/oscillation direction by the amount of amplitude. Accordingly, the position where secondary electrons 300 are emitted also similarly deviates in the direction contrary to the vibration/oscillation direction by the amount of amplitude. Therefore, it is necessary for the detectors 222 and 224 to perform detection at the position similarly deviated according to the deviated position where secondary electrons 300 are emitted. Accordingly, it is sufficient to be able to perform one axis operation that can shift the detectors 222 and 224 in the direction of detection position deviation, along the detection surface, similar to the deviation direction of the position where secondary electrons 300 are emitted.

A high voltage power supply circuit (not shown) is connected to the electron gun 201. The high voltage power supply circuit applies an acceleration voltage to between the cathode and the anode (not shown) in the electron gun 201. In addition to this applied acceleration voltage, by applying a predetermined bias voltage, and heating the cathode at a predetermined temperature, electrons emitted from the cathode are accelerated to become electron beams which are to be emitted. For example, electron lenses are used as the illumination lens 202, the reducing lens 205, and the objective lens 207, and all of them are controlled by the lens control circuit 124. In the blanking aperture array mechanism 204, a plurality of individual blanking mechanisms are arranged on the blanking substrate to be described later, and a control signal to each individual blanking mechanism is output from the blanking control circuit 126. The deflector 208 is configured by at least four electrodes, and controlled by the deflection control circuit 128.

In the case of the substrate 101 being a semiconductor wafer on which a plurality of chip (die) patterns are formed, pattern data of the chip (die) pattern is input from the outside the inspection apparatus 100 to the storage device 109 to be stored therein.

FIG. 1 shows configuration elements necessary for describing the first embodiment. It should be understood that other configuration elements generally necessary for the writing apparatus 100 may also be included therein.

Figure 2:
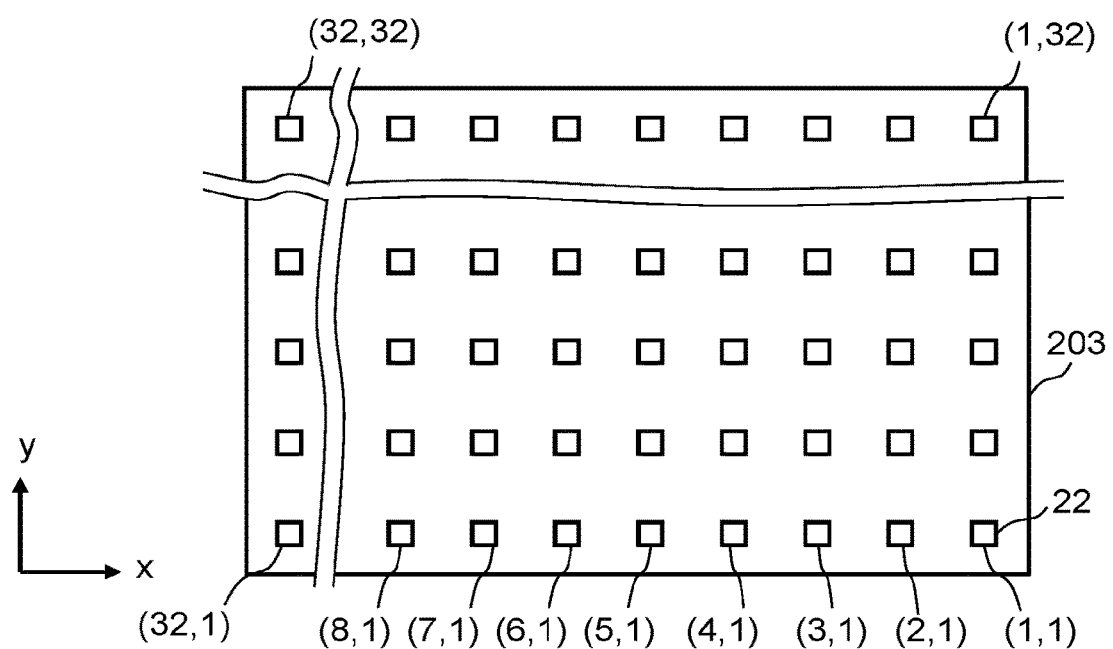
FIG. 2 is a conceptual diagram showing a configuration of a shaping aperture array member according to the first embodiment.

FIG. 2 is a conceptual diagram showing a configuration of a shaping aperture array member according to the first embodiment. As shown in FIG. 2, holes (openings) 22 of n columns wide (x direction) and m rows long (y direction) are two-dimensionally formed, like a matrix, at a predetermined arrangement pitch in the shaping aperture array member 203, where one of n and m is an integer of 1 or more, and the other is an integer of 2 or more. In FIG. 2, for example, holes 22 of 32 (columns in×direction)×32 (rows in y direction) are formed. Each of the holes 22 is a quadrangle of the same dimensional shape. Alternatively, each of the holes 22 can be a circle of the same circumference. Multi-beams 20 are formed by letting portions of an electron beam 200 individually pass through a corresponding hole of a plurality of holes 22. Here, the case in which the holes 22 of two or more rows and columns are arranged in both the x and y directions is shown, but the arrangement is not limited thereto. For example, it is also acceptable that a plurality of holes 22 are arranged in only one row (x direction) or in only one column (y direction). That is, in the case of only one row, a plurality of holes 22 are arranged in the x direction as a plurality of columns, and in the case of only one column, a plurality of holes 22 are arranged in the y direction as a plurality of rows. The method of arranging the holes 22 is not limited to the case of FIG. 2 where holes are arranged like a grid in the width and length directions. For example, with respect to the k-th and the (k+1)th rows arrayed in the length direction (y direction), each hole in the k-th row and each hole in the (k+1)th row may be mutually displaced in the width direction (x direction) by a dimension "a". Similarly, with respect to the (k+1)th and the (k+2)th rows arrayed in the length direction (y direction), each hole in the (k+1)th row and each hole in the (k+2)th row may be mutually displaced in the width direction (x direction) by a dimension "b". Alternatively, other configuration may be employed.

Figure 3:
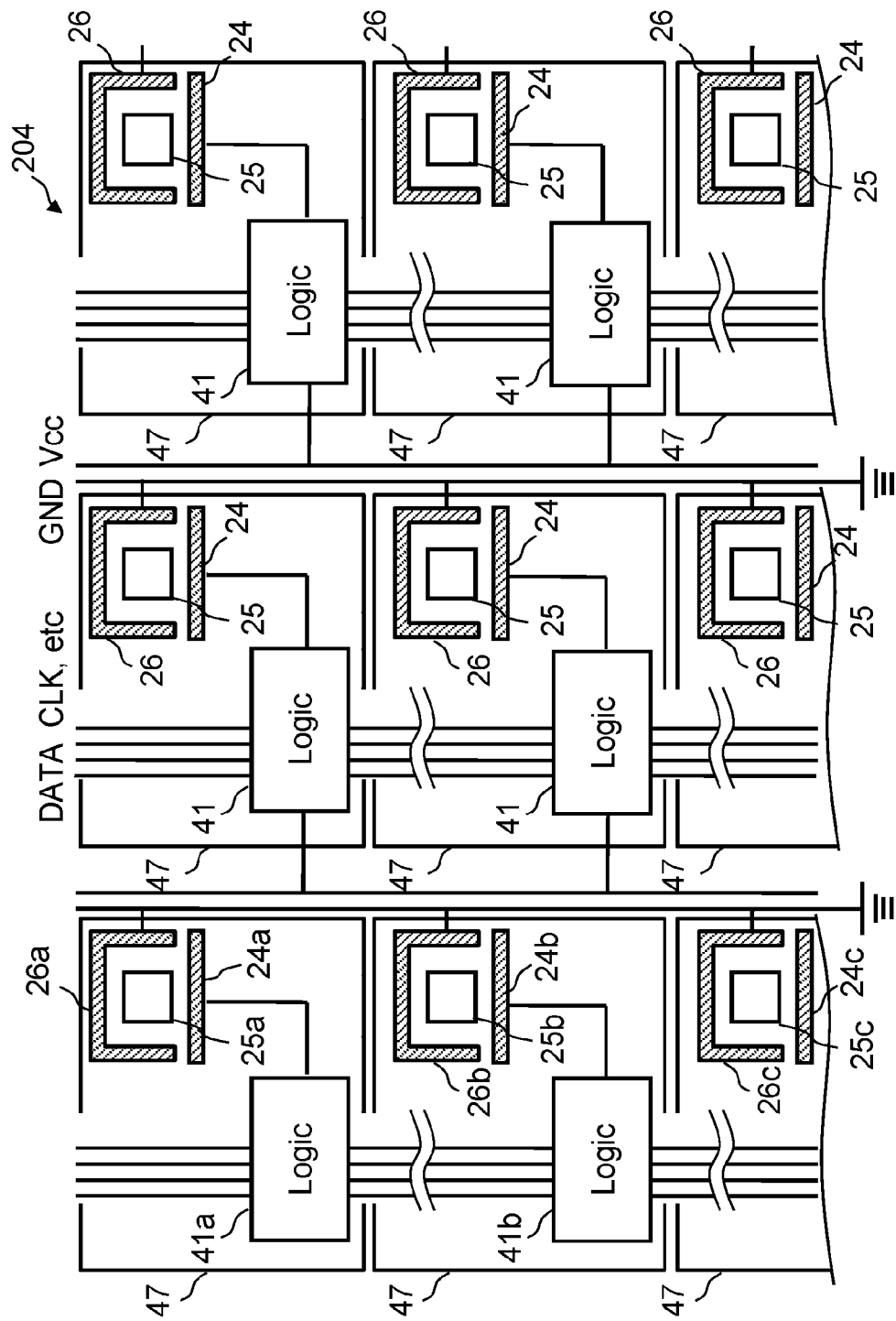
FIG. 3 is a top view conceptual diagram showing a part of a blanking aperture array mechanism according to the first embodiment.

FIG. 3 is a top view conceptual diagram showing apart of a blanking aperture array mechanism according to the first embodiment. In FIG. 3, the positional relation of electrodes 24 and 26, and that of a control circuit 41 are not in accordance with each other. As shown in FIG. 3, in the blanking aperture array mechanism 204, there are formed passage holes 25 (openings), through which multiple beams individually pass, at the positions each corresponding to each hole 22 of the shaping aperture array member 203 of FIG. 2, on a substrate (not shown) (e.g., silicon substrate). Then, a pair of electrodes 24 and 26 (blanker: blanking deflector) for blanking deflection is arranged close to each passage hole 25 on the substrate in a manner such that the electrodes 24 and 26 are opposite each other with respect to the passage hole 25 concerned. Moreover, close to each passage hole 25, there is arranged the control circuit 41 (logic circuit) for applying a deflection voltage to, for example, the electrode 24 for each passage hole 25. The other one (the electrode 26, for example) of the two electrodes 24 and 26 for each beam is grounded (earthed).

Further, a several (e.g., 5 to 10) bit line for control signal is connected to each control circuit 41. In addition to the several bit line, for example, a clock signal line, a power source line, and the like are connected to each control circuit 41. An individual blanking mechanism 47 composed of the electrodes 24 and 26 and the control circuit 41 is configured for each beam of multi-beams. A control signal for each control circuit 41 is output from the blanking control circuit 126. Moreover, a shift register (not shown) is arranged in each control circuit 41, and for example, shift registers for beams in one row of n×m multi-beams in the control circuit are connected in series. For example, control signals for beams in one row of n×m multi-beams are transmitted in series. For example, a control signal of each beam is stored in a corresponding control circuit 41 by n clock signals.

The electron beam 20 passing through a corresponding passage hole is deflected by a voltage independently applied to the two electrodes 24 and 26 being a pair. Blanking control is performed by this deflection. Blanking deflection is performed for each corresponding beam of multi-beams. Thus, each of a plurality of blankers performs blanking deflection of a corresponding beam of the multi-beams having passed through a plurality of holes 22 (openings) of the shaping aperture array member 203. By performing individual blanking control, an extraordinary beam can be excluded from the inspection.

Although the individual blanking mechanism 47 is shown in the example of FIG. 3, it is not limited thereto. A mechanism which collectively provide blanking control of the multi-beams 20 may also be employed.

Next, operations of the optical image acquisition unit 150 in the inspection apparatus 100 will be described. The electron beam 200 emitted from the electron gun 201 (emission unit) almost perpendicularly (e.g., vertically) illuminates the whole of the shaping aperture array member 203 by the illumination lens 202. A plurality of quadrangular holes (openings) are formed in the shaping aperture array member 203. The region including all the plurality of holes is irradiated with the electron beam 200. For example, a plurality of quadrangular electron beams (multi-beams) 20a to 20e are formed by letting portions of the electron beam 200, which irradiates the positions of a plurality of holes 22, individually pass through a corresponding hole of the plurality of holes of the shaping aperture array member 203. The multi-beams 20a to 20e individually pass through corresponding blankers (first deflector: individual blanking mechanism) of the blanking aperture array mechanism 204. Each blanker deflects (provides blanking deflection) the electron beam 20 which is individually passing.

The multi-beams 20a to 20e having passed through the blanking aperture array mechanism 204 are reduced by the reducing lens 205, and go toward the hole in the center of the limiting aperture member 206. At this stage, the electron beam 20 which was deflected by the blanker of the blanking aperture array mechanism 204 deviates (shifts) from the hole in the center of the limiting aperture member 206 and is blocked by the limiting aperture member 206. On the other hand, the electron beam 20 which was not deflected by the blanker of the blanking aperture array mechanism 204 passes through the hole in the center of the limiting aperture member 206 as shown in FIG. 1. Blanking control is provided by ON/OFF of the individual blanking mechanism so as to control ON/OFF of beams. Thus, the limiting aperture member 206 blocks each beam which was deflected to be in the OFF state by the individual blanking mechanism. Then, for each beam, one shot beam is formed by a beam which has been made during a period from becoming beam ON to becoming beam OFF and has passed through the limiting aperture member 206. The multi-beams 20 having passed through the limiting aperture member 206 are focused by the objective lens 207 so as to be a pattern image of a desired reduction ratio. Then, respective beams (the whole of the multi-beams 20) having passed through the limiting aperture member 206 are collectively deflected in the same direction by the deflector 208 in order to irradiate respective beam irradiation positions on the substrate 101. Ideally, the multi-beams 20 irradiating at a time are aligned at pitches obtained by multiplying the arrangement pitch of a plurality of holes of the shaping aperture array member 203 by a desired reduction ratio described above. Thus, the electron beam column 102 irradiates the substrate 101 with two-dimensional n×m multi-beams 20 at a time. Secondary electrons 300 being a flux of secondary electrons corresponding to each beam of the multi-beams 20, emitted from the substrate 101 because the multi-beams 20 irradiate desired positions of the substrate 101, are detected when being incident to a plurality of detectors 222 and 224. In other words, for each beam of the multi-beams 20, a plurality of detectors 222 and 224 detect secondary electrons 300 emitted from one position of the substrate 101, which is irradiated with one beam. Thereby, the information amount of detected data of each position of the substrate 101 can be increased.

Figure 4:
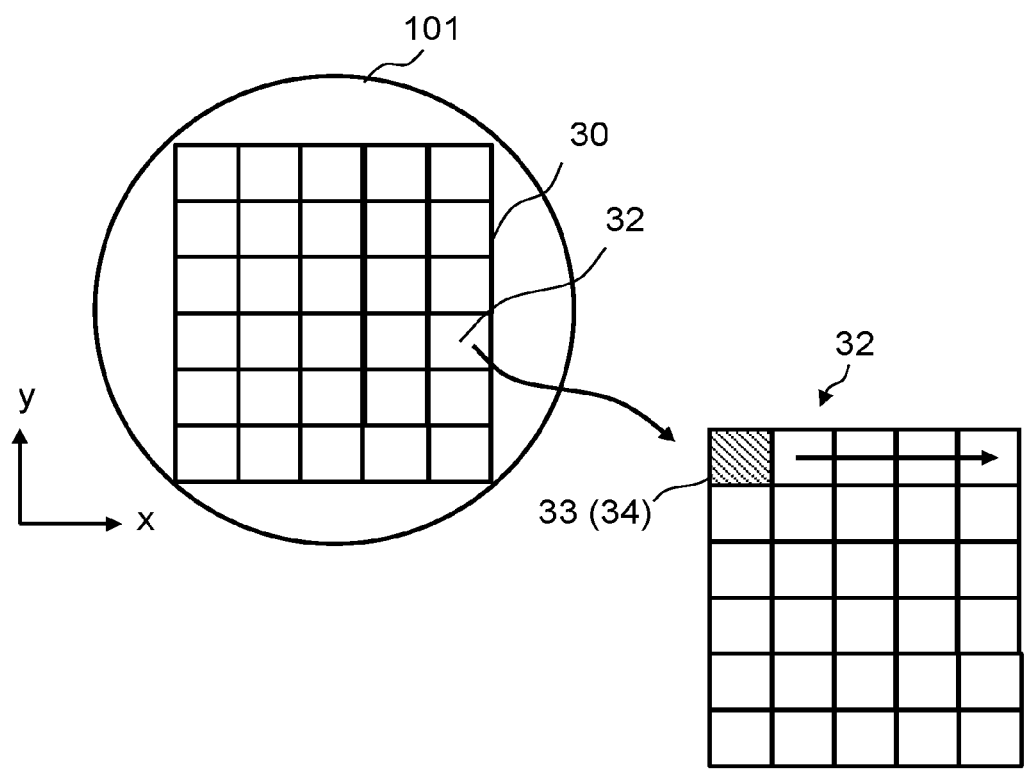
FIG. 4 is a conceptual diagram describing an example of a scanning operation according to the first embodiment.

FIG. 4 is a conceptual diagram describing an example of a scanning operation according to the first embodiment. As shown in FIG. 4, in an inspection region 30 of the substrate 101, there are formed a plurality of chips 32 (die) in an array, each having predetermined width and length in the x and y directions, for example. Each chip 32 is formed to be, for example, 30 mm×25 mm on the substrate 101. Pattern inspection is performed for each chip 32. For example, the region of each chip 32 is virtually divided into a plurality of unit inspection regions 33 by the width (x direction) and the length (y direction) being the same as the width and length of an irradiation region 34 which can be irradiated with one irradiation of the entire multi-beams 20. First, the XY stage 105 is moved to make an adjustment so that the irradiation region 34, which can be irradiated with one irradiation of the entire multi-beams 20, maybe located at the position of the unit inspection region 33 at one (e.g., upper left end) of the four corners of the first chip 32, and then, a scanning operation is started. According to the first embodiment, for example, by repeating a "step and repeat" operation, each unit inspection region 33 is scanned by the multi-beams 20 while the irradiation region 34 is shifted one by one in the x direction by the width of the irradiation region 34. After scanning all the unit inspection regions 33 in the same row in the x direction, where the rows are arrayed in the y direction, the stage position is moved in the y direction to similarly scan the unit inspection regions 33 aligned in the x direction in the next row by the multi-beams 20. This operation is repeated until scanning the region of one chip 32 is completed. Then, the XY stage 105 is moved to make an adjustment so that the irradiation region 34, which can be irradiated with one irradiation of the entire multi-beams 20, maybe be located at the position of the unit inspection region 33 at one (e.g., upper left end) of the four corners of the next chip 32, and then, another scanning operation is similarly performed. By repeating this operation, all the chips 32 can be scanned.

Figure 5:
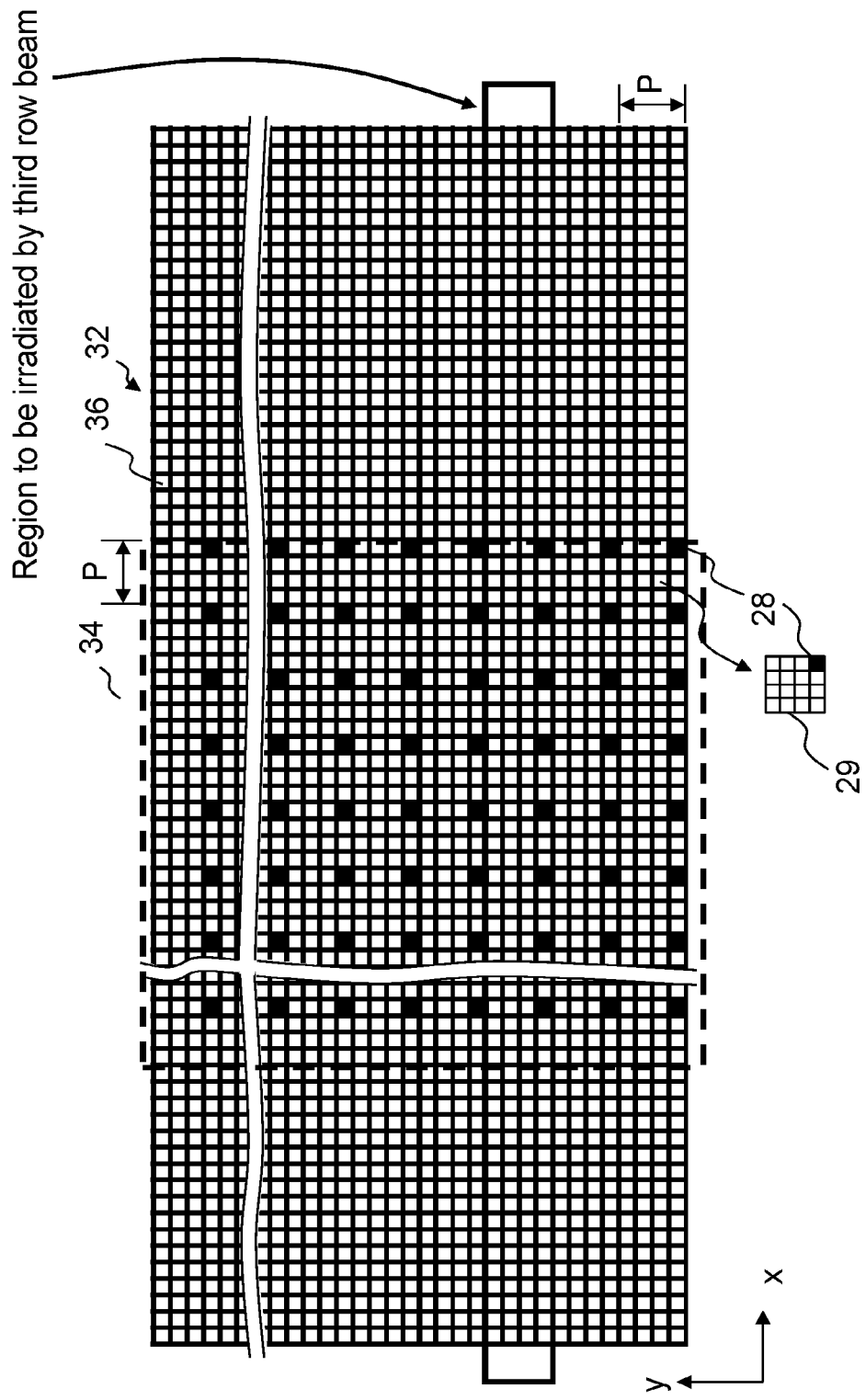
FIG. 5 shows an example of an irradiation region of multi-beams and a measurement pixel according to the first embodiment.

FIG. 5 shows an example of an irradiation region of multi-beams and a measurement pixel according to the first embodiment. In FIG. 5, the region of the chip 32 is divided into a plurality of mesh regions by the beam size of multi-beams, for example. Each mesh region serves as a measurement pixel 36 (unit irradiation region). In the irradiation region 34, there are shown a plurality of measurement pixels 28 (irradiation positions of beams of one shot) which can be irradiated with one irradiation of the multi-beams 20. In other words, the pitch between the adjacent measurement pixels 28 is a pitch P between beams of the multi-beams. In the example of FIG. 5, one grid 29 is a square region surrounded at four corners by four adjacent measurement pixels 28, and including one of the four measurement pixels 28. In the example of FIG. 5, each grid 29 is configured by 4×4 pixels.

Figure 6:
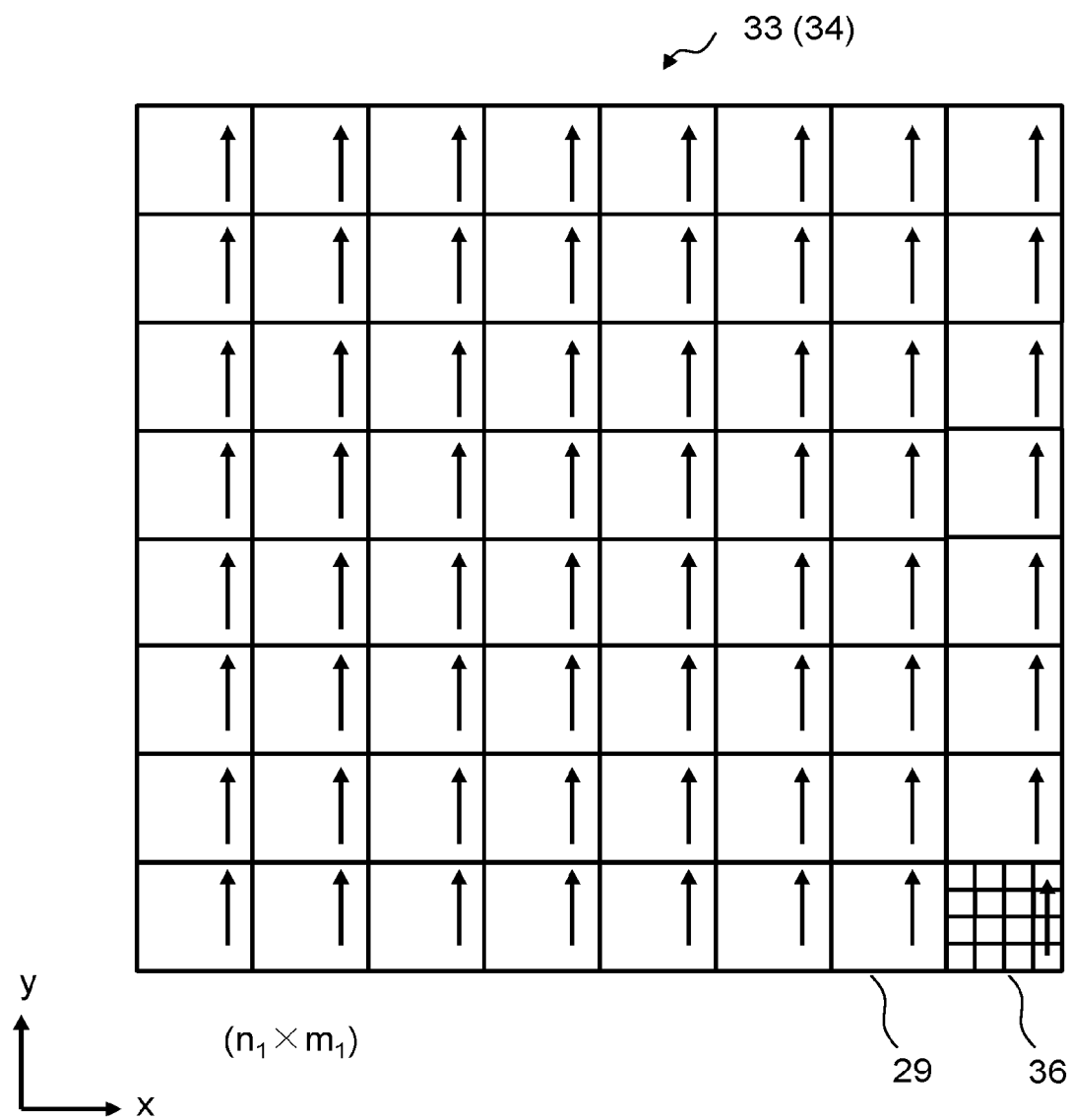
FIG. 6 is a conceptual diagram describing an example of details of a scanning operation according to the first embodiment.

FIG. 6 is a conceptual diagram describing an example of details of a scanning operation according to the first embodiment. FIG. 6 shows an example of scanning a certain unit inspection region 33 (irradiation region 34). In one irradiation region 34, there are arranged $n_1 \times m_1$ grids 29 in the x and y directions (two-dimensionally). When all the n×m multi-beams 20 are used, $n_1 \times m_1$ grids 29 indicate n×m grids 29. When the XY stage 105 is moved to a position where one unit inspection region 33 can be irradiated with the multi-beams 20, the XY stage 105 is stopped at the position, and then, the inside of the unit inspection region 33 concerned is scanned while regarding the unit inspection region 33 concerned as the irradiation region 34. Each beam of the multi-beams 20 takes charge of one grid 29 different from others. At the time of each shot, each beam irradiates one measurement pixel 28 equivalent to the same position in the grid 29 concerned. In the case of FIG. 6, the first shot of each beam irradiates the first measurement pixel 36 from the right in the bottom row in the grid 29 concerned. Then, the beam deflection position is shifted in the y direction by one measurement pixel 36 by collectively deflecting the entire multi-beams 20 by the deflector 208, the second shot irradiates the first measurement pixel 36 from the right in the second row from the bottom in the grid 29 concerned. Similarly, the third shot irradiates the first measurement pixel 36 from the right in the third row from the bottom in the grid 29 concerned. The fourth shot irradiates the first measurement pixel 36 from the right in the fourth row from the bottom in the grid 29 concerned. Next, the beam deflection position is shifted to the position of the second measurement pixel 36 from the right in the bottom row by collectively deflecting the entire multi-beams 20 by the deflector 208, the measurement pixel 36 is similarly irradiated in order in the y direction. By repeating this operation, all the measurement pixels 36 in one grid 29 are irradiated in order with one beam. In a one-time shot, the secondary electrons 300 being a flux of secondary electrons corresponding to a plurality of shots whose number is at maximum the same as that of a plurality of holes 22 are detected at a time by the multi-beams formed by passing through the plurality of holes 22 of the shaping aperture array member 203.

As described above, the entire multi-beams 20 scans the unit inspection region 33 as the irradiation region 34, and i.e. each beam individually scans one corresponding grid 29. In a state in which the XY stage 105 remains stopped, after scanning one unit inspection region 33 is completed, the irradiation region 34 moves to a next adjoining unit inspection region 33 by the step operation in order to scan the next adjoining unit inspection region 33 while the XY stage 105 remains stopped. Thus, the "step and repeat" operation is repeated to proceed scanning each chip 32. Due to shot of multi-beams, the secondary electrons 300 are emitted, at each time of the shot, circumferentially upward from the irradiated measurement pixel 36 so as to be detected by a plurality of detectors 222 and 224. Each of the plurality of detectors 222 and 224 detects, for each measurement pixel 36 (or each grid 29), the secondary electrons 300 emitted in the same direction in the secondary electrons 300 emitted circumferentially upward from each irradiated measurement pixel 36.

By performing scanning using the multi-beams 20 as described above, the scanning operation (measurement) can be performed at a higher speed than scanning by a single beam.

Although beam ON/OFF is performed for each 36 in the example described above, it is not limited thereto. Scanning may be performed, for each grid 29, by continuous beam while the grid 29 concerned is scanned by a corresponding beam. In other words, it may be beam OFF during the step operation.

Figure 7:
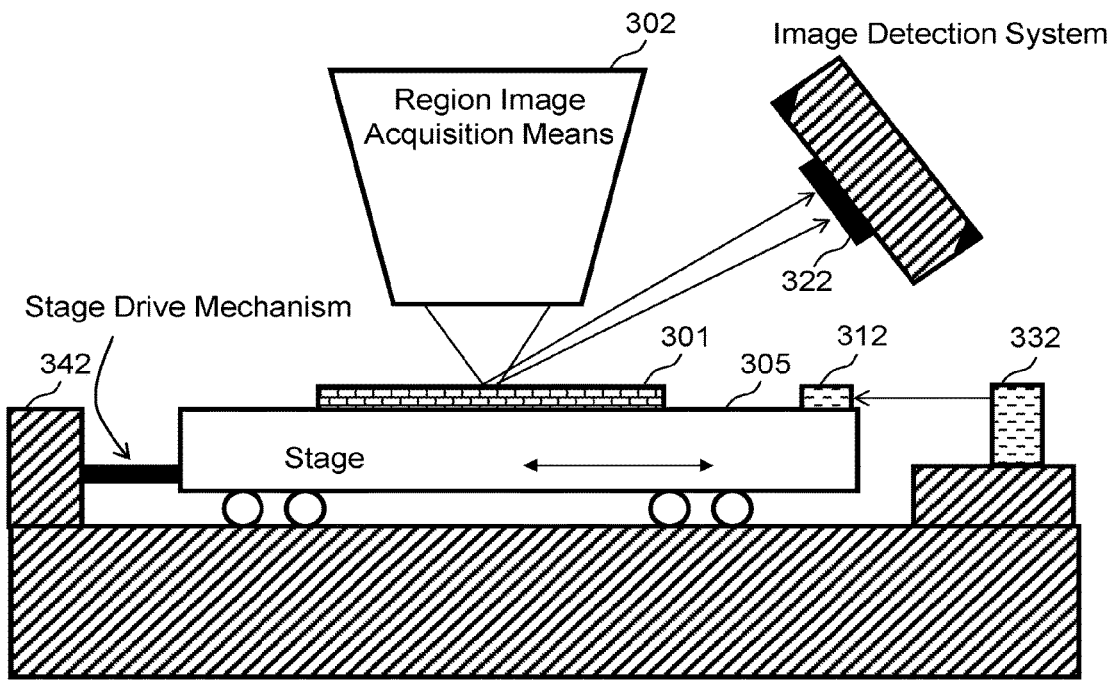
FIG. 7 shows an example of a structure of an image detection mechanism according to a comparative example to the first embodiment.

FIG. 7 shows an example of a structure of an image detection mechanism according to a comparative example to the first embodiment. In FIG. 7, a stage 305 is arranged on the base, and the stage 305 is moved in accordance with a "step and repeat" operation by a stage drive device 342. The position of the stage 305 is measured by a laser interferometer 332 which uses a mirror 312 on the stage 305. A column 302 irradiates a substrate 301 to be inspected on the stage 305 with an electron beam while the stage 305 is stopped, and an image detector 322 detects a secondary electron from the substrate 301 to be inspected. In FIG. 7, the image detector 322 is fixed.

Figure 8:
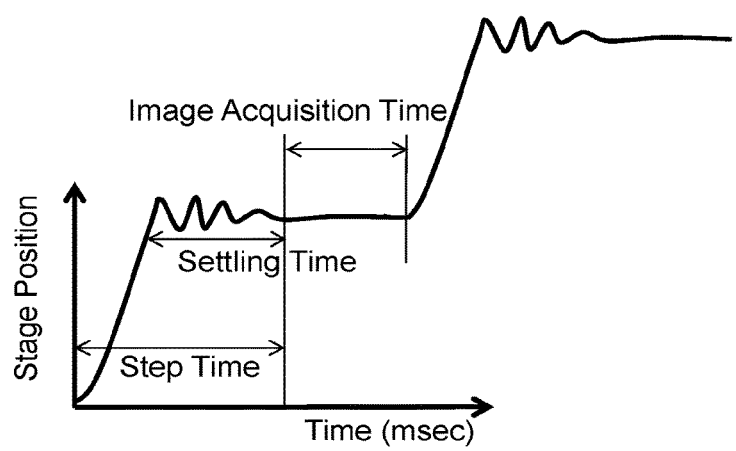
FIG. 8 shows a stage position distribution according to a comparative example to the first embodiment.

FIG. 8 shows a stage position distribution according to the comparative example to the first embodiment. As described above, the inspection substrate 301 of the comparative example to the first embodiment is arranged on the heavy stage 305. Moreover, as described above, since almost the whole surface of the inspection substrate 301 needs to be inspected, the stage 305 moves a long stroke distance. With respect to such a stage, such as the stage 305, which is heavy and moves through a long stroke, it takes time for statically settling (stabilizing) the stage 305 to stop at a position within a predetermined accuracy after the step movement of the stage as shown in FIG. 8. Therefore, as described above, there is a problem in the comparative example in that the time obtained by "the number of times of step-and-repeat movement"ב"settling time" is needed as a useless time during which no actual inspection is performed.

Figure 9:
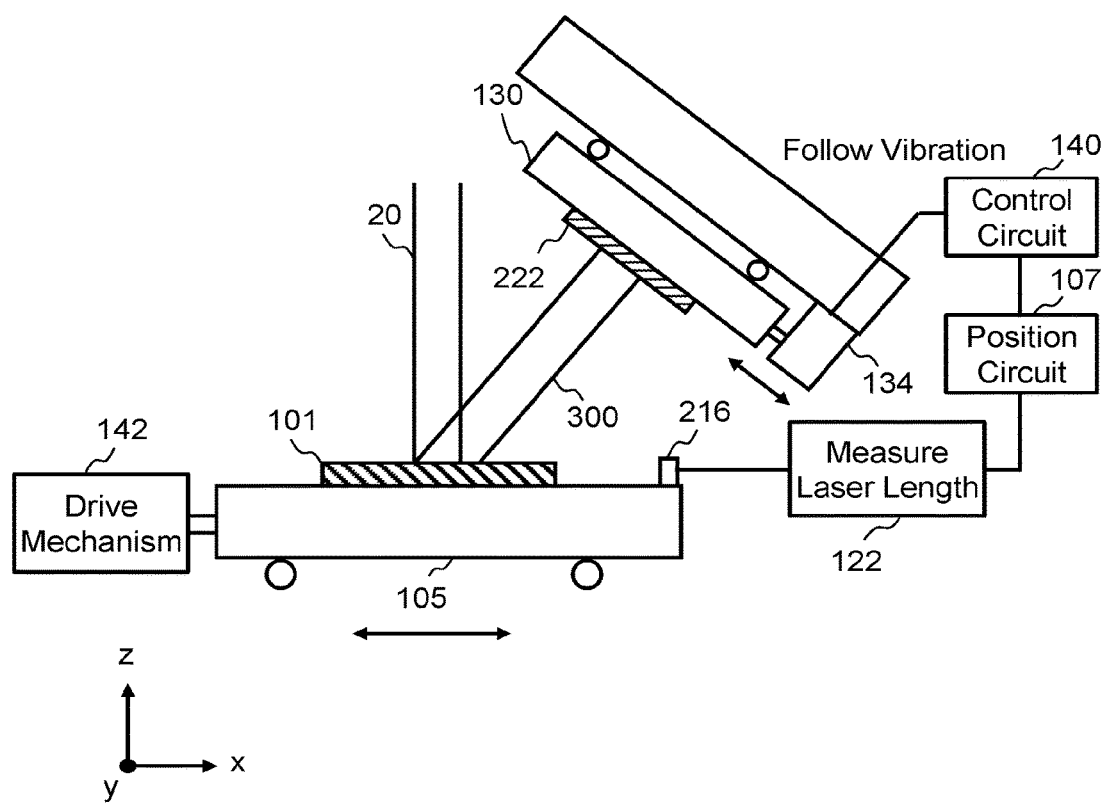
FIG. 9 shows an example of a structure of an image detection mechanism according to the first embodiment.

FIG. 9 shows an example of a structure of an image detection mechanism according to the first embodiment. FIG. 9 shows a part of the structure illustrated in FIG. 1. As described above, according to the first embodiment, when performing beam scanning in each chip 32, the XY stage 105 performs a "step and repeat" operation for each unit inspection region 33. The XY stage 105 is stopped at a position where the unit inspection region 33 concerned is located in the irradiation region 34, and the electron beam column 102 (column) scans the substrate 101, on which patterns are formed, with the multi-beams 20 composed of a plurality of electron beams. A plurality of detectors 222 and 224 detect secondary electrons emitted from the irradiated substrate 101 due to irradiation with the multi-beams 20. However, according to the first embodiment, unlike the comparative example shown in FIG. 8, a scanning operation is started during the settling time. Therefore, according to the first embodiment, each of a plurality of drive mechanisms 134 and 136 moves a corresponding detector 222 (or detector 224) in a plurality of detectors 222 and 224 in order to follow the movement of the XY stage 105. Specifically, each of a plurality of drive mechanisms 134 and 136 moves a corresponding detector 222 (or detector 224) in a plurality of detectors 222 and 224 in order to follow the vibration/oscillation of the XY stage 105 until the XY stage is settled (stabilized) in stopping in the "step and repeat" operation. Vibration of the XY stage 105 is measured by the laser length measurement system 122 (laser interferometer). Measured vibration data (position information) of the XY stage 105 is output to the position circuit 107, and then, to the detection position control circuit 140 from the position circuit 107. The detection position control circuit 140 controls a plurality of drive mechanisms 134 and 136 in order to move a corresponding detector 222 (or detector 224) in a plurality of detectors 222 and 224 such that a plurality of drive mechanisms 134 and 136 follow the vibration of the XY stage 105 by using the vibration data measured by the laser length measurement system 122.

For example, now is described the case where a plurality of detectors 222 and 224 are arranged at positions opposite each other in the x direction with respect to the optical axis, and the step movement of the XY stage 105 moves in the −x direction. If the XY stage 105 vibrates in the −x direction by x1, the irradiation position of multi-beams deviates (shifts) in the x direction by x1 compared to the design irradiation position. Position information indicated by an emitted secondary electron naturally becomes position information shifted in the x direction by x1 compared to the design irradiation position. If the detector 222 located in the x direction from the optical axis has been in a fixed state, it detects the secondary electron of a deviated position for information on the design irradiation position. Therefore, in FIG. 9 (FIG. 1), the drive mechanism 134 deviates (shifts) the detection position of the detector 222 obliquely downward by x1 along the detection surface by moving the detector stage 130 obliquely upward. Thereby, the detector 222 can detect the secondary electron at the position deviated obliquely downward (x direction of the detection surface) from the design irradiation position by x1 along the detection surface. On the other hand, if the detector 224 located in the −x direction from the optical axis has been in a fixed state, it detects the secondary electron at the deviated position for information on the design irradiation position. Therefore, in FIG. 1, the drive mechanism 136 deviates (shifts) the detection position of the detector 224 obliquely upward by x1 along the detection surface by moving the detector stage 132 obliquely downward. Thereby, the detector 224 can detect the secondary electron at the position deviated obliquely upward (x direction of the detection surface) from the design irradiation position by x1 along the detection surface.

By contrast, if the XY stage 105 vibrates in the x direction by x2, the irradiation position of multi-beams deviates (shifts) in the −x direction by x2 compared to the design irradiation position. Position information indicated by an emitted secondary electron naturally becomes position information shifted in the −x direction by x2 compared to the design irradiation position. If the detector 222 located in the x direction from the optical axis has been in a fixed state, it detects the secondary electron at the deviated position for information on the design irradiation position. Therefore, in FIG. 9 (FIG. 1), the drive mechanism 134 deviates the detection position of the detector 222 obliquely upward by −x2 along the detection surface by moving the detector stage 130 obliquely downward. Thereby, the detector 222 can detect the secondary electron at the position deviated obliquely upward (−x direction of the detection surface) from the design irradiation position by −x2 along the detection surface. On the other hand, if the detector 224 located in the −x direction from the optical axis has been in a fixed state, it detects the secondary electron at the deviated position for information on the design irradiation position. Therefore, in FIG. 1, the drive mechanism 136 deviates the detection position of the detector 224 obliquely downward by −x2 along the detection surface by moving the detector stage 132 obliquely upward. Thereby, the detector 224 can detect the secondary electron at the position deviated obliquely downward (−x direction of the detection surface) from the design irradiation position by −x2 along the detection surface.

Figure 10:
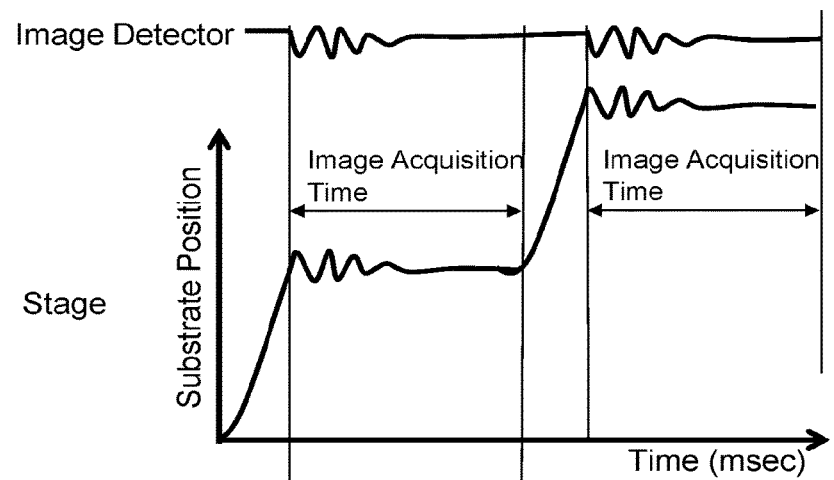
FIGS. 10A to 10C are time charts showing a relation among a detector position, a stage position, and a substrate position according to the first embodiment.

FIGS. 10A to 10C are time charts showing a relation among a detector position, a stage position, and a substrate position according to the first embodiment. When the XY stage 105 reaches the end position of a step movement, the XY stage 105 is attenuated to be stopped by the drive mechanism 142, etc. In that case, the XY stage 105 vibrates as shown in FIG. 10B. This vibration time serves as a settling time. However, according to the first embodiment, as shown in FIG. 10A, a plurality of detectors 222 and 224 move (shift) to follow in accordance with the vibration of the XY stage 105. A plurality of detectors 222 and 224 move in a predetermined direction depending on their arrangement positions so that a secondary electron emitted from the irradiation position on the substrate 101 deviated by the vibration may be detected by the detector at the position similarly deviated. Consequently, the relative position between the XY stage 105 and the detector 222 (relative position between the XY stage 105 and the detector 224) can be maintained under a halt condition. Therefore, as shown in FIG. 10C, a scanning operation (image acquisition) can be performed from the starting time of settling in stopping the XY stage 105. Thus, the scanning operation (image acquisition) time can be overlapped with the settling time in stopping the XY stage 105. Accordingly, it is possible to reduce the time in which inspection cannot be performed because of the "step and repeat" operation.

In a step of multi-beam scanning and a secondary electron detecting, as described above, the optical image acquisition unit 150, using the multi-beams 20 in which a plurality of electron beams are arranged at a predetermined pitch P, scans the inspection substrate 101 on which a plurality of figure patterns are formed, and detects the secondary electrons 300 emitted from the irradiated inspection substrate 101 due to irradiation with the multi-beams 20. The method for scanning and the method for detecting the secondary electrons 300 have already been described above. Detected data on the secondary electrons 300 from each measurement pixel 36 detected by the detectors 222 and 224 is output to the detection circuit 106 in order of measurement. In the detection circuit 106, the detected data in analog form is converted into digital data by an A-D converter (not shown), and stored in the chip pattern memory 123. Then, at the stage when detected data for one chip 32 has been accumulated, the accumulated detected data is transmitted as chip pattern data to the comparison circuit 108, with information on each position from the position circuit 107.

On the other hand, in parallel or in tandem with the step of multi-beam scanning and the secondary electron detecting, a reference image is formed (generated).

In a reference image generation step, if the substrate 101 is a semiconductor substrate, a reference image generation unit, such as the development circuit 111 and the reference circuit 112, generates a reference image of a region corresponding to a measurement image (optical image) of the grid 29 configured by a plurality of pixels 36, based on exposure image data defining an exposure image on the substrate used when a mask pattern of an exposure mask is exposed and transferred onto the semiconductor substrate. Instead of the exposure image data, writing data (design data) may be used which is base for forming an exposure mask to expose and transfer a plurality of figure patterns onto the substrate 101. If the substrate 101 is an exposure mask, the reference image generation unit, such as the development circuit 111 and the reference circuit 112, generates a reference image of a region corresponding to a measurement image (optical image) of the grid 29 configured by a plurality of pixels 36, based on writing data (design data) which is base for forming a plurality of figure patterns on the substrate 101. An optical image may be generated by making its resolution lower than that of an image in units of grids 29, as an image in units of unit inspection regions 33 in which one grid 29 is one pixel. In such a case, a reference image can be similarly generated by making its resolution lower than that of an image in units of grids 29, as an image in units of unit inspection regions 33 in which one grid 29 is one pixel. In the case of the grid 29 being one pixel, the pattern occupancy in the grid 29 can be a gray scale value.

Specifically, it operates as follows: First, the development circuit 111 reads writing data (or exposure image data) from the storage device 109 through the control computer 110, converts each figure pattern of each irradiation region 34 defined in the read writing data (or exposure image data) into image data of binary values or multiple values, and transmits this image data to the reference circuit 112.

Here, basics of figures defined by writing data (or exposure image data) are, for example, rectangles or triangles. For example, there is stored figure data defining the shape, size, position, and the like of each pattern figure by using information, such as coordinates (x, y) of the reference position of the figure, lengths of sides of the figure, and a figure code serving as an identifier for identifying the figure type such as a rectangle, a triangle and the like.

When writing data (or exposure image data) used as figure data is input to the development circuit 111, the data is developed into data of each figure. Then, figure codes, figure dimensions and the like indicating figure shapes in the figure data are interpreted. Then, the development circuit 111 develops design image data of binary values or multiple values, as a pattern to be arranged in a square in units of grids of predetermined quantization dimensions, and outputs the developed data. In other words, the development circuit 111 reads design data, calculates the occupancy rate occupied by figures in a design pattern for each square obtained by virtually dividing an inspection region into squares in units of predetermined dimensions, and outputs n-bit occupancy rate data. For example, it is preferable that one square is set as one pixel. If one pixel has a resolution of $1/2^8$ (=1/256), 1/256 small regions, whose number is the same as that of figure regions arranged in a pixel, are allocated in order to calculate the occupancy rate in the pixel. Then, the calculated rate is output as 8-bit occupancy rate data to the reference circuit 112. The size of the square can preferably be the same as that of the measurement pixel 36. If the grid 29 is one pixel, the square size may be the same as that of the grid 29.

The reference circuit 112 performs appropriate filter processing on design image data being transmitted image data of a figure. Since the measurement data as an optical image obtained from the detection circuit 106 is in the state affected by the filtering by the electron optical system, in other words, in the analog state continuously changing, it is possible to match the design image data with the measurement data by also performing filter processing on the design image data being image data on the design side whose image intensity (gray value) is represented by digital values. In this manner, a design image (reference image) to be compared with a measurement image (optical image) of the grid 29 is generated. The generated image data of the reference image is input into the comparison circuit 108 to be stored in the memory.

Figure 11:
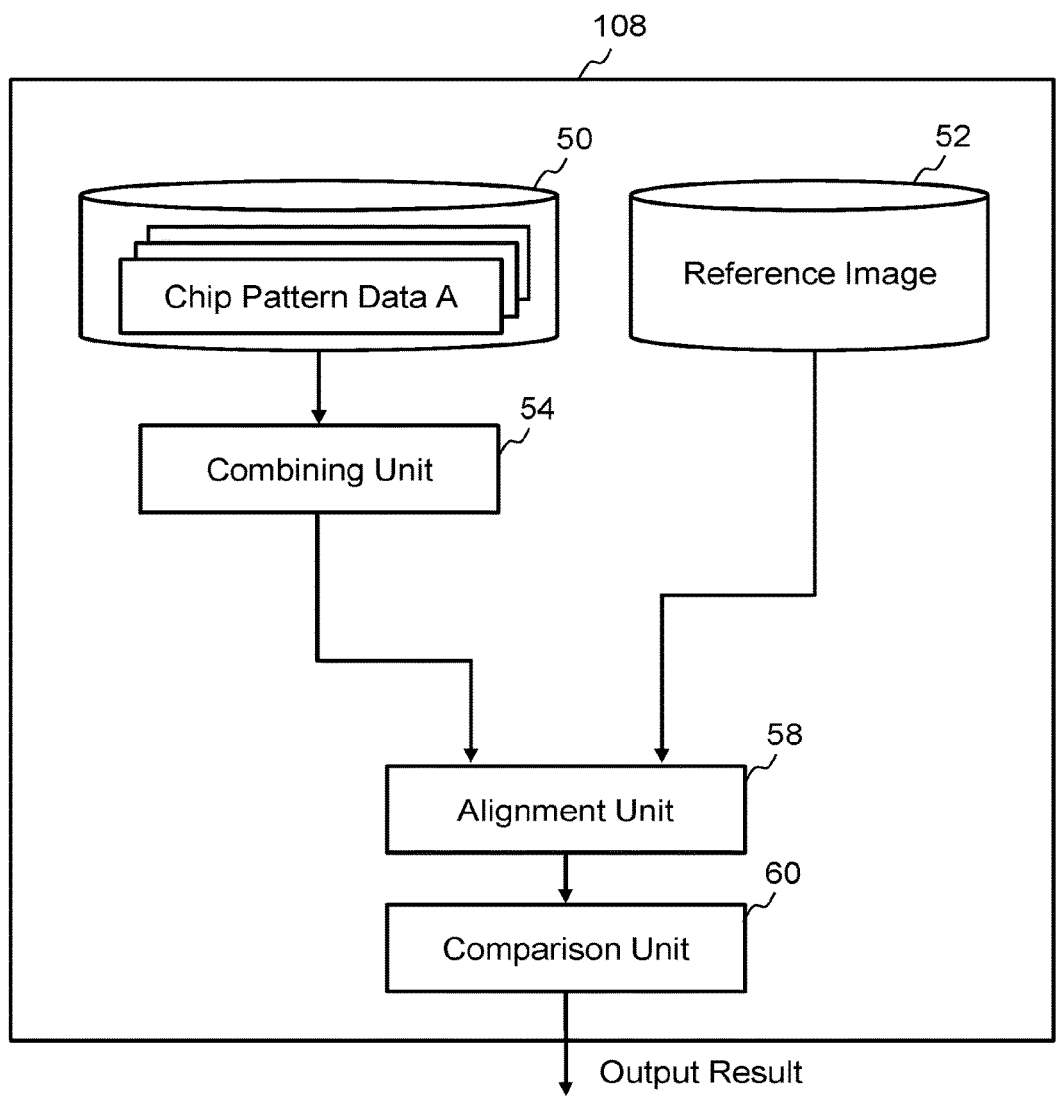
FIG. 11 shows an internal configuration of a comparison circuit according to the first embodiment.

FIG. 11 shows an internal configuration of a comparison circuit according to the first embodiment. In FIG. 11, storage devices 50 and 52, such as magnetic disk drives, a combining unit 54, an alignment unit 58, and a comparison unit 60 are arranged in the comparison circuit 108. Each of the "units" such as the combining unit 54, the alignment unit 58, and the comparison unit 60 includes a processing circuitry. As the processing circuitry, for example, an electric circuit, computer, processor, circuit board, quantum circuit, or semiconductor device may be used. Each of the "units" may use a common processing circuitry (same processing circuitry), or different processing circuitries (separate processing circuitries). Input data required in the combining unit 54, the alignment unit 58, and the comparison unit 60, and calculated results are stored in a memory (not shown) each time.

Chip pattern data transmitted from each of the detectors 222 and 224 is temporarily stored in the storage device 50, with information indicating each position from the position circuit 107. Similarly, reference image data is temporarily stored in the storage device 52, with information indicating each design position. According to the first embodiment, a plurality of detectors 222 and 224 detect the secondary electrons 300 emitted from the same position on the substrate 101. Then, the combining unit 54 (an example of an image generation processing circuit) combines each data detected by a plurality of detectors 222 and 224, and generates an image of a pattern. By using a plurality of detectors, the amount of information is larger than that of data detected by a single detector, and therefore, a highly precise two-dimensional image can be generated. Alternatively, since the amount of information is large, a three-dimensional image may be generated. When an optical image is a three-dimensional image, a reference image should also be a three-dimensional image.

Next, the alignment unit 58 provides positioning between an optical image (measurement image) and a reference image, using units of sub pixels each smaller than the pixel 36. For example, positioning may be performed by a least-square method.

The comparison unit 60 compares the optical image concerned and the reference image for each pixel 36. The comparison unit 60 compares both the images for each pixel 36, based on predetermined determination conditions in order to determine whether there is a defect, such as a shape defect. For example, if a gradation value difference of each pixel 36 is larger than a determination threshold Th, it is determined that there is a defect. Then, the comparison result is output, and specifically, output to the storage device 109, monitor 117, or memory 118, or alternatively, output from the printer 119. In the case of the grid 29 being a pixel, the pixel 36 should be read as the grid 29.

As described above, according to the first embodiment, it is possible in pattern inspection using electron beams to reduce the time in which inspection cannot be performed because of the "step and repeat" operation. Therefore, inspection time can be shortened.

In the above description, each ". . . circuit" includes a processing circuitry. As the processing circuitry, for example, an electric circuit, computer, processor, circuit board, quantum circuit, semiconductor device, or the like can be used. Each ". . . circuit" may use a common processing circuitry (same processing circuitry), or different processing circuitries (separate processing circuitries). A program for causing a computer to execute the processor and the like can be stored in a recording medium, such as a magnetic disk drive, magnetic tape drive, FD, ROM (Read Only Memory), etc.

Embodiments have been explained referring to specific examples described above. However, the present invention is not limited to these specific examples. Although, in the case described above, a plurality of detectors 222 and 224 detect the secondary electrons 300 emitted from the same position on the substrate 101, it is not limited thereto. A single detector may also be used for detection when it is acceptable that the amount of information on each position on the substrate 101 is decreased, or when the secondary electrons 300 emitted from the same position on the substrate 101 can be loaded in one direction by the magnetic field, electric field, or the like of the optical system.

While the apparatus configuration, control method, and the like not directly necessary for explaining the present invention are not described, some or all of them can be selectively used on a case-by-case basis when needed.

In addition, any other pattern inspection apparatus and method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
a column configured to scan a substrate on which a pattern is formed, using multi-beams composed of a plurality of electron beams;
a stage configured to mount the substrate thereon and to be movable;
a detector configured to detect secondary electrons emitted from the substrate because the substrate is irradiated with the multi-beams; and
a drive mechanism configured to move the detector in order to follow movement of the stage.

2. The apparatus according to claim 1, wherein the stage performs a step and repeat operation, and the drive mechanism moves the detector in order to follow vibration of the stage until the stage is settled in a case where the stage is stopped in the step and repeat operation.

3. The apparatus according to claim 2, further comprising:
a laser interference apparatus configured to measure the vibration of the stage,
wherein the drive mechanism moves the detector by using vibration data measured by the laser interference apparatus.

4. The apparatus according to claim 1, wherein a detection surface of the detector is arranged to be inclined with respect to a surface of the substrate.

5. The apparatus according to claim 1, further comprising:
a detector stage configured to mount the detector thereon,
wherein the drive mechanism moves the detector stage on which the detector has been placed.

6. A pattern inspection apparatus comprising:
a column configured to scan a substrate on which a pattern is formed, using multi-beams composed of a plurality of electron beams;
a stage configured to mount the substrate thereon and to be movable;
a plurality of detectors each configured to detect secondary electrons emitted from the substrate because the substrate is irradiated with the multi-beams;
a plurality of drive mechanisms each configured to move a corresponding detector of the plurality of detectors in order to follow movement of the stage; and
an image generation processing circuitry configured to combine each data detected by the plurality of detectors and to generate an image of the pattern.

7. The apparatus according to claim 6, wherein the stage performs a step and repeat operation, and the plurality of drive mechanisms move the plurality of detectors in order to follow vibration of the stage until the stage is settled in a case where the stage is stopped in the step and repeat operation.

8. The apparatus according to claim 7, further comprising:
a laser interference apparatus configured to measure the vibration of the stage,
wherein each of the plurality of drive mechanisms moves the corresponding detector of the plurality of detectors by using vibration data measured by the laser interference apparatus.

9. The apparatus according to claim 6, wherein a detection surface of each of the plurality of detectors is arranged to be inclined with respect to a surface of the substrate.

10. The apparatus according to claim 6, further comprising:
a plurality of detector stages each configured to mount a corresponding detector of the plurality of detectors thereon,
wherein each of the plurality of drive mechanisms moves a corresponding detector stage in the plurality of detector stages in a state where the corresponding detector in the plurality of detectors has been placed on the corresponding detector stage of the plurality of detector stages.

* * * * *